United States Patent [19]

Averill

[11] Patent Number: 4,770,660

[45] Date of Patent: Sep. 13, 1988

[54] FEMORAL PROSTHESIS WITH SELECTIVELY REMOVABLE COLLAR

[75] Inventor: Robert G. Averill, Ringwood, N.J.

[73] Assignee: Osteonics Corp., Allendale, N.J.

[21] Appl. No.: 4,524

[22] Filed: Jan. 20, 1987

[51] Int. Cl.[4] ............................................. A61F 2/36
[52] U.S. Cl. ...................................................... 623/23
[58] Field of Search ...................... 623/23, 22, 16, 18, 623/20

[56] References Cited

U.S. PATENT DOCUMENTS

| | | | |
|---|---|---|---|
| 4,012,796 | 3/1977 | Weisman et al. | 623/23 X |
| 4,016,606 | 4/1977 | Murray et al. | 623/20 |
| 4,112,522 | 9/1978 | Dadurian et al. | 623/18 |
| 4,608,053 | 8/1986 | Keller | 623/23 |
| 4,623,353 | 11/1986 | Buechel et al. | 623/23 |
| 4,698,063 | 10/1967 | Link et al. | 623/23 |

Primary Examiner—Ronald L. Frinks
Attorney, Agent, or Firm—Samuelson & Jacob

[57] ABSTRACT

A stem-type femoral prosthesis has a calcar collar selectively installed on the stem of the prosthesis or removed from the stem interoperatively by sliding the collar in transverse directions between the medial and lateral sides of the stem, at the proximal end of the stem, to facilitate seating of the stem without the collar during implant and to enable subsequent removal of stem by first releasing the collar from the stem to gain access to the affixed surfaces of the stem beneath the collar.

9 Claims, 2 Drawing Sheets

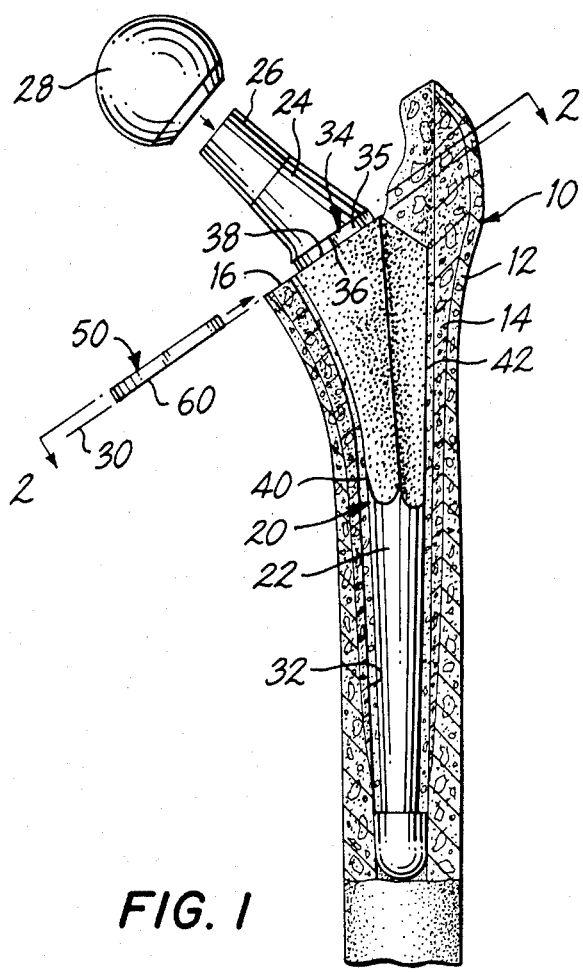
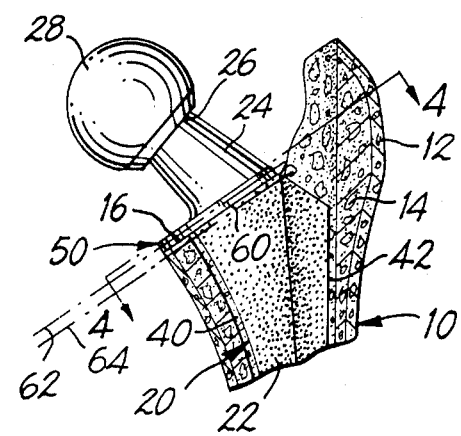
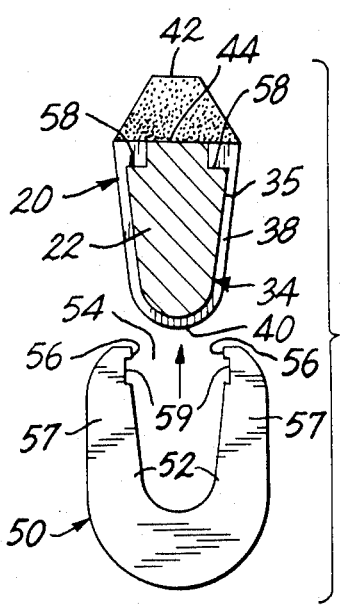
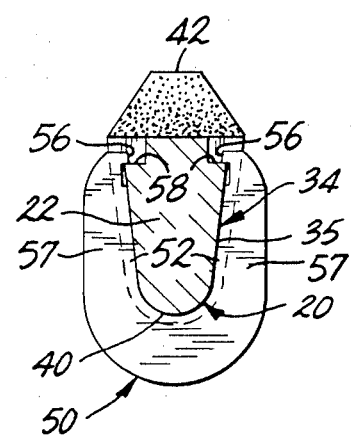
FIG. 1
FIG. 3
FIG. 2
FIG. 4

FEMORAL PROSTHESIS WITH SELECTIVELY REMOVABLE COLLAR

The present invention relates generally to prosthetic implant devices and pertains, more specifically, to a femoral prosthesis of the type having a stem and a collar.

It has been demonstrated that the incorporation of a collar in a stem-type femoral prosthesis provides advantages in that fixation of the prosthesis can be enhanced and the load-bearing ability of the prosthesis is improved. Accordingly, a variety of stem-type femoral prostheses having collars currently are available and are used regularly in hip joint replacement. However, the presence of a collar on the prosthesis presents certain disadvantages, both from the standpoint of proper seating of the prosthesis during implant and subsequent removal of the prosthesis, should such removal become necessary.

Proper seating of a collared stem-type femoral prosthesis requires careful preparation of the proximal femur to assure that the resection level will enable appropriate seating of the stem within the cancellous bone, as well as proper location and seating of the collar upon the calcar. A high cut can result in the seating of the collar before the stem can become fully seated, thereby affecting fixation of the stem. A low cut can result in seating of the stem before the collar can become fully seated, thereby largely defeating the purpose of the collar. In addition, the collar tends to block visual determination of the appropriate seating of the prosthesis during the implant procedure. The above holds true whether fixation is to be accomplished with or without cement.

Should later revision become necessary, removal of the prosthesis is impeded by the presence of a collar since the collar prevents the passage of cutting instruments between the stem of the prosthesis and the cortical shell of the femur. That problem is discussed fully in U.S. Pat. No. 4,623,353, which discloses a modification of a unitary collar for the purpose of addressing the problem.

In the present invention, a stem-type femoral prosthesis includes a collar which is selectively assembled with the stem and selectively removed from the stem, interoperatively, in such a manner as to provide the advantages of a collared prosthesis without the disadvantages, as outlined above. Among the objects and advantages of the present invention are the following: The stem of the prosthesis may be fitted and seated, without the presence of the collar, and concomitant obstruction, for accurate determination of fit, alignment and seating; any inaccuracies in initial resection level can be compensated for subsequent to proper seating of the stem to assure proper seating of the collar as well; in any later revision, the collar can be removed from the stem to enable ease of dislodging the stem for removal of the prosthesis; selection can be made from a variety of stems and collars to arrive at an optimum combination of stem and collar for a particular implant; and an increased range of styles and fit is made available with relative economy.

The above objects, as well as further objects and advantages, are attained by the present invention which may be described briefly as a stem-type femoral prosthesis for implantation in a resected proximal end of a femur, the prosthesis comprising: a stem having a proximal end, and a distal end spaced axially from the proximal end; a transverse collar for placement in a proximal location adjacent the proximal end of the stem to engage the resected proximal end of the femur when the stem is in an appropriately seated position in the femur upon implantation of the prosthesis; securing means enabling selective securement of the collar at the proximal location and selective release of the collar from the proximal location for interoperative installation and removal of the collar subsequent to seating of the stem in the seated position, the securing means including complementary interengageable elements on the stem and on the collar, the complementary interengageable elements being oriented relative to the proximal end of the stem to enable transverse sliding of the collar relative to the stem into and out of the proximal location and into and out of securement at the proximal location in response to the transverse sliding of the collar relative to the stem into and out of the proximal location for interoperative installation and removal of the collar, the complementary interengagable elements including engaging surfaces for precluding unwanted axial and transverse relative movement between the collar and the stem when the collar is secured to the stem at the proximal location.

The invention will be understood more fully, while still further objects and advantages will become apparent, in the following detailed description of preferred embodiments illustrated in the accompanying drawing, in which:

FIG. 1 is a partially exploded, partially cross-sectioned elevational view showing a prosthesis constructed in accordance with the present invention being implanted in a resected femur;

FIG. 2 is a plan view of a portion of FIG. 1, partially cross-sectioned along line 2—2 of FIG. 1;

FIG. 3 is a fragmentary view of a portion of FIG. 1, but with the component parts assembled;

FIG. 4 is a cross-sectional view taken along line 4—4 of FIG. 3;

Figure 5:
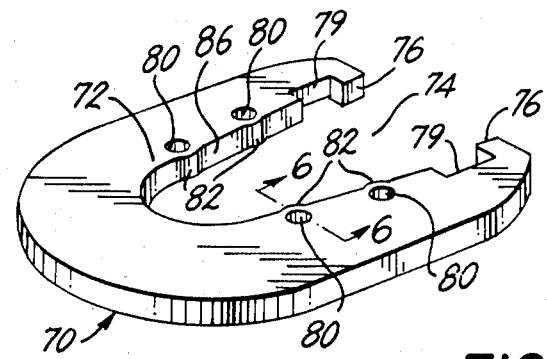
FIG. 5 is a perspective view of an alternate collar, illustrating another embodiment of the invention.

Referring now to the drawing, and especially to FIGS. 1 and 2 thereof, the proximal end of a femur 10 has been resected in preparation for the implant of a femoral prosthesis. Femur 10 includes an outer shell of cortical bone 12, inner cancellous bone 14 and calcar 16. A femoral prosthesis, constructed in accordance with the invention, is illustrated at 20 and is shown being implanted at the prepared proximal end of femur 10.

Femoral prosthesis 20 is of the type having a stem 22 which is inserted into the femur 10 to be affixed to the femur 10 so that a prosthetic portion 24 which is unitary with the stem 22 at the proximal end of the stem 22 of the prosthesis 20 will provide a neck 26 upon which is placed a spherical head 28 for engagement with either the natural acetabulum or an acetabular prosthesis for articulation in a hip replacement. The femur 10 is prepared to receive prosthesis 20 by cutting to establish a neck resection level at 30 and then creating a passage 32 within the femur 10 for receiving the stem 22 of the prosthesis 20. The distal end of the stem 22 is inserted into passage 32 and advanced axially until the stem is seated fully within passage 32.

A recess in the form of a groove 34 is placed within prosthesis 20, between stem 22 and prosthetic portion 24. Groove 34 is recessed within prosthesis 20, having an inner surface 35 and confronting upper and lower surfaces 36 and 38, respectively, and extends transversely across the prosthesis 20 in the direction from the medial side 40 of the prosthesis 20 toward the lateral side 42. As best seen in FIG. 2, groove 34 has a generally U-shaped profile configuration oriented such that the mouth 44 of the U-shaped configuration faces toward the lateral side 42 of the prosthesis. The U-shaped profile configuration tapers outwardly from the medial side 40 toward the lateral side 42.

When the preparation of the femur 10 has been carried out accurately, appropriate seating of the stem 22 within passage 32 will place lower surface 38 of groove 34 flush with the resection level 30. A separate collar 50 is then installed by sliding the collar 50 into the groove 34 in the transverse direction from the medial side 40 toward the lateral side 42. Collar 50 includes an inner rim portion 52 having a U-shaped profile configuration with mouth 54, all generally complementary with the U-shaped profile configuration of groove 34 so that inner rim portion 52 fits snugly into groove 34 to secure collar 50 against axial movements relative to stem 22.

Turning now to FIGS. 3 and 4, when the prosthesis 20 is assembled, collar 50 is secured by detent elements which include opposed latches 56 projecting inwardly toward one another at the mouth 54 of the U-shaped profile configuration of inner rim portion 52 and opposite shoulders 58, at the lateral side 42 of the prosthesis 20, adjacent the mouth 44 of the U-shaped profile configuration of groove 34. During assembly, the latches 56 ride along inner surface 35 of groove 34 and, by virtue of the projection of latches 56 inwardly toward one another into the mouth 54 of the U-shaped profile configuration of inner rim portion 52, the taper of the U-shaped profile configuration of groove 34, the axial confinement of latches 56 between the upper and lower surfaces 36 and 38 of groove 34, and the cantilever action of the arms 57 of the configuration of collar 50, the latches 56 are urged outwardly, away from one another, against the elastic bias of the material of collar 50, until the inner rim portion 52 is fully engaged with groove 34 at which point the latches 56 pass over the inner surface 35 and are urged into engagement with shoulders 58, along the complementary engaged surfaces of the latches 56 and shoulders 58, to capture the collar 50 within groove 34. In this manner, collar 50 is secured in place in response to the transverse sliding of the collar 50 into full engagement with the groove 34. A small relief area 59 is provided at each latch 56 to assure proper operation and to enable ease of manufacture. Collar 50 is constructed of metal and the securing mechanism described above relies upon the elastic properties of the material of the collar 50 itself for proper operation.

By assuring that the lower surface 38 of groove 34 is flush with the resection level 30, the inferior surface 60 of collar 50 will be flush with the calcar 16 and collar 50 will be seated properly. Since the collar 50 is not assembled with the stem 22 until after the stem 22 is seated properly in the femur 10, inaccuracies in the location of the resection level 30 relative to the groove 34 (and ultimate collar location) can be observed before the collar 50 is placed in the groove 34 and adjustments can be made to assure appropriate seating of the collar 50 upon the calcar 16. Thus, where the resection level has been formed by a high cut, as illustrated in phantom at 62 in FIG. 3, the calcar 16 may be trimmed subsequent to insertion and seating of the stem 22 to bring the resection level down to the lower surface 38 of groove 34. Alternately, collar 50 may be provided with an inferior surface 60 offset upwardly from the lower surface 38 so that the upwardly offset inferior surface (not shown) will be flush with the calcar 16. Should the resection level 30 be below the lower surface 38 of groove 34, as a result of a low cut, as shown in phantom at 64, collar 50 may be provided with an inferior surface 60 offset downwardly from the lower surface 38 so that the downwardly offset inferior surface (not shown) will be flush with the calcar 16. Once the collar 50 is installed, head 28 may be secured to neck 26 to complete the prosthesis 20.

Should it become necessary to remove the prosthesis 20 after implant, collar 50 can be released and removed from stem 22 to expose the portion of the calcar 16 beneath the collar 50 and enable a cutting instrument to be passed between the stem 22 and the shell of cortical bone 12 to loosen the stem 22 for removal. Collar 50 is released and removed merely by reversing the assembly procedure set forth above. Latches 56 are urged outwardly away from one another against the elastic bias of the material of collar 50 until the latches 56 are disengaged from shoulders 58. Collar 50 then is moved in the transverse direction from the lateral side 42 toward the medial side 40 until inner rim portion 52 and collar 50 are withdrawn from groove 34.

It will be apparent that the provision of the separate collar 50 which is selectively installed or removed from the stem 22 of the stem-type femoral prosthesis 20 attains the aforementioned advantages in implant procedures and in subsequent removal of the prosthesis. The availability of a separate collar 50 also enables the choice of any one of a variety of collar configurations and surfaces independent of the stem configuration. Thus, collar 50 may be provided with variations in overall configuration as well as an inferior surface which is plain, coated or enhanced in any desired manner to provide for fixation of the collar 50 to the femur 10 upon completion of the implant.

Figure 6:
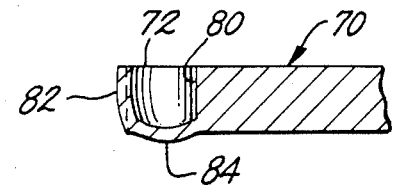
FIG. 6 is an enlarged cross-sectional view taken along line 6—6 of FIG. 5.

Once the collar 50 is installed within the groove 34 it is important that the collar 50 become fully integrated with the stem 22; that is, there must be no relative movement between the collar 50 and the stem 22 and the collar 50 must be capable of enhancing the load-bearing capabilities of the prosthesis 20, the same as in prostheses where a collar and stem are unitary. While the relative dimensions of the inner rim portion 52 and the complementary surfaces of groove 34 can be machined to tolerances close enough to attain the desired integration, one practical approach is to provide compensating means to compensate for any variations in these relative dimensions so that the desired integration is assured. In the embodiment illustrated in FIGS. 5 and 6, an alternate collar 70 has an inner rim portion 72 with a U-shaped profile configuration, tapered outwardly slightly toward the mouth 74 of the profile configuration, and latches 76 at the mouth 74, with adjacent relief areas 79. A plurality of blind holes 80 are spaced along inner rim portion 72 and extend axially into the material of collar 70. Material immediately adjacent each blind hole 80 is upset to establish permanently deformed, somewhat resilient bulged protrusions including inwardly projecting protrusions 82 and downwardly projecting protrusions 84. Upon assembly of collar 80 within groove 34, any looseness in fit resulting from the spacing between upper and lower surfaces 36 and 38 relative to the axial thickness of inner rim portion 72 is taken up by protrusions 84. Likewise, any looseness in fit resulting from the relative dimensions of inner surface 35 of groove 34 and the complementary inner surface 86 of inner rim portion 72 is taken up by protrusions 82. In this manner, relative movements between stem 22 and the installed collar 70 are precluded and the collar 70 is fully integrated with the stem 22.

It is to be understood that the above detailed description of embodiments of the invention is provided by way of example only. Various details of design and construction may be modified without departing from the true spirit and scope of the invention as set forth in the appended claims.

The embodiments of the inventor in which an exclusive property or privilege is claimed are defined as follows:

1. A stem-type femoral prosthesis for implantation in a resected proximal end of a femur, said prosthesis comprising:
    a stem having a proximal end, and a distal end spaced axially from the proximal end;
    a transverse collar for placement in a proximal location adjacent the proximal end of the stem to engage the resected proximal end of the femur when the stem is in an appropriately seated position in the femur upon implantation of the prosthesis;
    securing means enabling selective securement of the collar at said proximal location and selective release of the collar from said proximal location for interoperative installation and removal of the collar subsequent to seating of the stem in said seated position, said securing means including complementary interengageable elements on the stem and on the collar, said complementary interengageable elements being oriented relative to the proximal end of the stem to enable transverse sliding of the collar relative to the stem into and out of the proximal location and said securing means including detent means for effecting securement of the collar at said proximal location and release of the collar from said proximal location in response to said transverse sliding of the collar relative to the stem into and out of said proximal location for said interoperative installation and removal of the collar, said complementary interengageable elements and said detent means including engaging surfaces for precluding unwanted axial and transverse relative movement between the collar and the stem when the collar is secured to the stem at the proximal location.

2. The invention of claim 1 wherein the interengaging elements include a recess in the stem and a collar portion complementary to the recess for engagement therein.

3. The invention of claim 2 wherein the recess includes a groove in the stem, the groove extending in the direction from the medial side to the lateral side of the stem, and the collar portion includes an inner rim portion engageable within the groove.

4. The invention of claim 3 including compensating means in said inner rim portion for compensating for any variations in the relative dimensions of the groove and the inner rim portion so as to further secure the collar and the stem against relative movement.

5. The invention of claim 3 wherein the groove has a generally U-shaped configuration including a mouth facing toward the lateral side of the stem, and the inner rim portion of the collar has a generally U-shaped configuration and a mouth essentially complementary to the U-shaped configuration and mouth of the groove.

6. The invention of claim 5 wherein said detent means include first detent elements in the stem adjacent the mouth of the U-shaped configuration of the groove, and second detent elements in the collar adjacent the mouth of the U-shaped configuration of the inner rim portion of the collar, the second detent elements being complementary to the first detent elements for engagement of the first and second detent elements to secure the collar in said proximal location.

7. The invention of claim 6 wherein the second detent elements include opposed latch members projecting toward one another adjacent the mouth of the U-shaped configuration of the inner rim portion of the collar and the first detent elements include shoulders at the lateral side of the stem, adjacent the mouth of the U-shaped configuration of the groove.

8. The invention of claim 7 wherein the latch members are unitary with the collar and are biased toward one another by the U-shaped configuration of the collar.

9. The invention of claim 8 including compensating means in said inner rim portion for compensating for any variations in the relative dimensions of the groove and the inner rim portion so as to further secure the collar and the stem against relative movement.

* * * * *